US00PP36091P2

(12) United States Plant Patent
Barendse

(10) Patent No.: US PP36,091 P2
(45) Date of Patent: Sep. 3, 2024

(54) ***RHODODENDRON* PLANT NAMED 'AZAARE03'**

(50) Latin Name: ***Rhododendron* hybrid**
Varietal Denomination: AZAARE03

(71) Applicants: Kwekerij Arends Paterswolde B.V., Paterswolde (NL); Loviflowers BV, Moerbeke-Waas (BE)

(72) Inventor: Matthijs C. Barendse, Paterswolde (NL)

(73) Assignees: KWEKERIJ ARENDS PATERSWOLDE B.V., Paterswolde (NL), part interest; LOVIFLOWERS BV, Moerbeke-Waas (BE), part interest ( * ) Notice: Subject to any disclaimer, the term of this patent is extended or adjusted under 35 U.S.C. 154(b) by 0 days.

(21) Appl. No.: 18/101,077

(22) Filed: Jan. 24, 2023

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 5/02; A01H 5/00
See application file for complete search history.

(56) References Cited

PUBLICATIONS

In re Wingen; Feb. 2, 2023; 9 pages.*
https://www.youtube.com/watch?v=y6dpceNbVBs; Oct. 18, 2018; 1 page.*
https://www.bloemenkrant.nl/nieuws/algemeen/81908/nomiaties-show-your-colours-award-ipm-2023-bekend; Jan. 13, 2023; 2 pages.*
https://www-soll--galabau-de.translate.goog/aktuelle-news/ansicht-aktuelles/datum/2021/05/14/stylische-azalee-erobert-gaerten-und-kuebel.html?_x_tr_sl=de&_x_tr_tl=en&_x_tr_hl=en&_x_tr_pto=sc; May 14, 2021; 2 pages.*
Screenshot of a portion of the video https:www.youtube.com/watch?v=y6dpceNBVBs; Oct. 18, 2018.*
PLUTO UPOVROM Plant Variety Database Citation for 'AZAARE03' as per GB 17/34; May 1, 2022; 1 page.*

* cited by examiner

*Primary Examiner* — Kent L Bell
(74) *Attorney, Agent, or Firm* — Penny J. Aguirre

(57) ABSTRACT

A new cultivar of hybrid *Rhododendron* plant named 'AZAARE03' that is characterized by its uniform and compact plant habit, its floriferous blooming habit, its dense branching habit, its inflorescences with petals that are non-overlapping resulting in a star-shaped appearance, its clearly visible stamens and pollen, its flowers that are white in color, and its leaves that are narrow and long in size.

2 Drawing Sheets

Botanical classification: *Rhododendron* hybrid.
Cultivar designation: 'AZAARE03'.

CROSS REFERENCE TO A RELATED APPLICATIONS

This application is related to a European plant breeders' rights application filed on Oct. 27, 2021, application No. 2021/2569 and to a plant breeders' right application filed in The United Kingdom on Apr. 30, 2022, Application No. 17/34. The Applicant received the information for the Plant breeders' rights applications directly from the Inventor. This application is also co-pending with a U.S. Plant Patent Applications filed for plants derived from the same breeding program that are entitled *Rhododendron* Plant Named 'AZAARE02' (U.S. Plant patent application Ser. No. 18/101,066) and *Rhododendron* Plant Named 'AZAARE01' (U.S. Plant patent application Ser. No. 18/101,058).

BACKGROUND OF THE INVENTION

The present invention relates to a new and distinct cultivar of *Rhododendron* plant of hybrid origin, botanically known as *Rhododendron* 'AZAARE03' and will be referred to hereafter by its cultivar name, 'AZAARE03'. 'AZAARE03' is a new cultivar of *Rhododendron* shrub grown for use as a landscape plant.

The new invention arose from an ongoing controlled breeding program in Paterswolde, The Netherlands. A goal of the breeding program was to develop hybrid cultivars of *Rhododendron* with flowers with unique shapes and colors.

The Inventor made a controlled cross in 2010 in a test garden in Paterswolde, The Netherlands between an unnamed plant from the Inventor's breeding program as the female parent (designated as ref no. 1802) and *Rhododendron simsi* 'Polarstern' (not patented) as the male parent. 'AZAARE03' was selected in 2016 as a single unique plant amongst the resulting seedlings.

Asexual propagation of the new cultivar was first accomplished by stem cuttings in Paterswolde, The Netherlands in 2016 under the direction the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of 'AZAARE03'. These attributes in combination distinguish 'AZAARE03' as a new and distinct cultivar of *Rhododendron*.

1. 'AZAARE03' exhibits a uniform and compact plant habit.
2. 'AZAARE03' exhibits a floriferous blooming habit.
3. 'AZAARE03' exhibits a dense branching habit
4. 'AZAARE03' exhibits inflorescences with petals that are non-overlapping resulting in a star-shaped appearance.
5. 'AZAARE03' exhibits clearly visible stamens and pollen.
6. 'AZAARE03' exhibits flowers that are white in color.
7. 'AZAARE03' exhibits leaves that are narrow and long in size.

The female parent of 'AZAARE03' differs from 'AZAARE03' in having a less compact and more open and less uniform plant habit and inflorescences that lack the star-shaped appearance of 'AZAARE03'. The male parent of 'AZAARE03' differs from 'AZAARE03' in having inflorescences that are not star-shaped in appearance. 'AZAARE03' can also be most closely compared to the *Rhododendron* cultivars 'Kinku Saku' (U.S. Plant Pat. No. 17,177), 'AZAARE01' and 'AZAARE02'. 'Kinku Saku' is similar to 'AZAARE03' in having flowers with a similar shape. 'Kinku Saku' differs from 'AZAARE03' in having flowers that are pink in color, flower petals that are touching, a later flowering period, and a less compact plant habit. 'AZAARE01' and 'AZAARE02' are similar to 'AZAARE03' in plant size and in having flowers that are non-overlapping. 'AZAARE01' differs from 'AZAARE03' in having flowers that are bright pink in color. 'AZAARE02' differs from 'AZAARE03' in having flowers that are bright lilac in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by Thompson-Morgan and Cowell's Garden Center.

BRIEF DESCRIPTION OF THE DRAWINGS

The accompanying color photographs illustrate the overall appearance and distinct characteristics of the new *Rhododendron*. The plant in the photograph is 20-months in age as grown outdoors with 3 plugs in a 19-cm container in Moerbeke, Belgium.

The photograph in FIG. 1 provides a side view of 'AZAARE03' in bloom.

Figure 1:
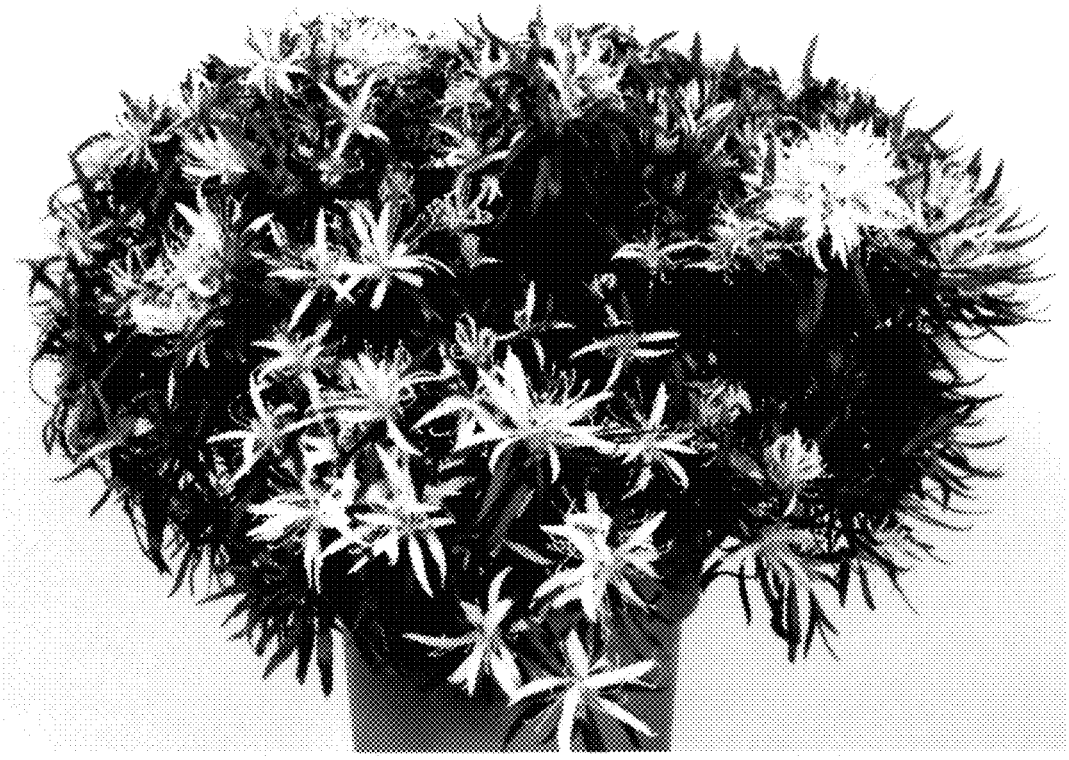
Figure 2:
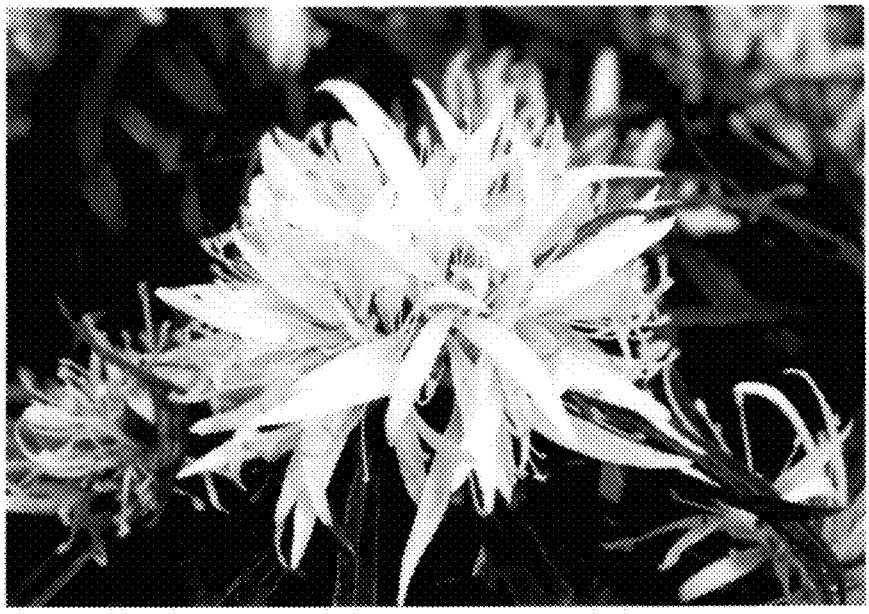

The photograph in FIG. 2 provides a close-up view of the inflorescences of 'AZAARE03'.

Figure 3:
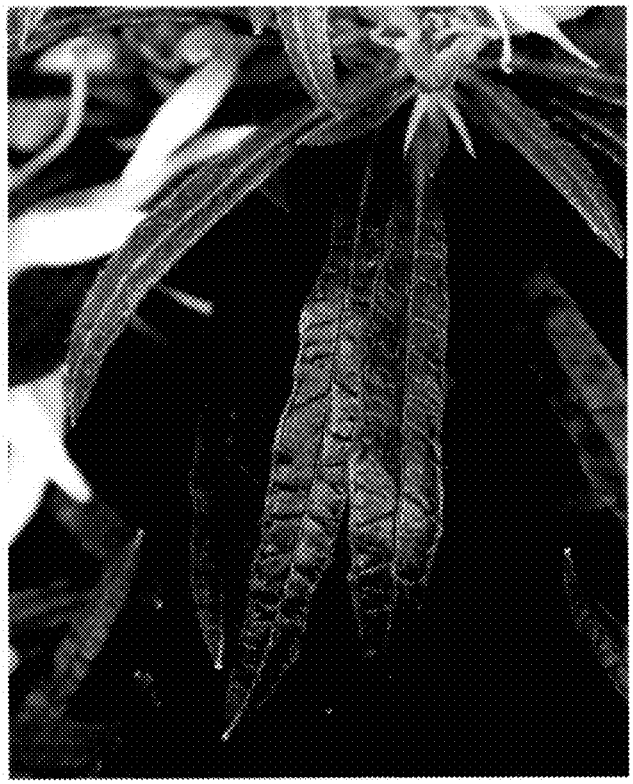

The photograph in FIG. 3 provides a close-up view of the foliage of 'AZAARE03'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 20-month-old plants of the new cultivar as grown outdoors with 3 plugs in a 19-cm container in Moerbeke, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period.*—April to May in The Netherlands.
*Plant type.*—Evergreen shrub.
*Plant habit.*—Dense, uniform growth, and compact plant habit.
*Height and spread.*—26.4 cm in height, 35.5 cm in diameter as grown with 3 plugs in a 19-cm container, reaches 50 cm in height and spread in the landscape.
*Hardiness.*—At least in U.S.D.A. Zones 8 to 12.
*Diseases and pests.*—No susceptibility or resistance to pests or diseases has been observed.
*Root description.*—Fibrous.
*Propagation.*—Stem cuttings.
*Growth rate.*—Moderate to high.
*Root development.*—4 weeks for root initiation and 1.5 years to produce a marketable plant from a rooted cutting.

Stem description:

*Shape.*—Round.
*Stem color.*—Young; 151A, mature; 165A, older stems and bark; 165A, N199B and N199C.
*Stem size.*—Lateral; an average of 7.6 cm in length, 2 mm in diameter.
*Stem surface.*—Very slightly glossy.
*Stem aspect.*—Average of 45° (varying between 40° and 50°).
*Stem strength.*—Strong.
*Branching.*—Densely branched, 7 main branches, 30 lateral branches.
*Internode length.*—5 mm.

Foliage description:

*Leaf shape.*—Narrow oblong to narrow oblanceolate.
*Leaf division.*—Simple.
*Leaf base.*—Attenuate.
*Leaf apex.*—Acute.
*Leaf venation.*—Anastomosing, upper surface; 146A in color, lower surface; N148C to N148D in color.
*Leaf margins.*—Finely repand, moderately revolute and finely undulate.
*Leaf attachment.*—Petiolate.
*Leaf arrangement.*—Alternate, leaf clusters whorled at terminal shoot apex.
*Leaf orientation.*—Horizontal, sometimes curved slightly upward or downward.
*Leaf aspect.*—Flat to very slightly wavy (lamina).
*Leaf surface.*—Upper surface moderately glossy, lower surface very slightly glossy, upper surface and margins of leaves moderately covered with short hairs, average of 1 mm in length, too small to measure color, lower surface sparsely to moderately covered with very short hairs; average of 0.5 mm in length, too small to measure color.

*Leaf color*.—Young leaves upper surface; a blend of 143A and 146A, young leaves lower surface; N144D, mature and fall leaves upper surface; a blend of 147A and N189A, tip 145B, mature and fall leaves lower surface; 139C, tipped 145B.

*Leaf size*.—Average of 4.7 cm in length, 6 mm in width.

*Petioles*.—Average of 7 mm in length and 1.5 mm in diameter, strong, upper surface color 145A, lower surface color N144B, both surfaces slightly glossy and moderately covered with short hairs; 2 mm in length and N170B in color.

Flower description:

*Inflorescence type*.—Axillary and terminal clusters.

*Lastingness of flowers*.—Average of 10 days.

*Inflorescence size*.—Average of 3.6 cm in height and 5.8 cm in diameter.

*Flower quantity*.—Average of 3 per inflorescence, 80 per plant.

*Flower size*.—An average of 5.4 cm in in diameter and 2.4 cm in height.

*Flower fragrance*.—None.

*Flower type*.—Rotate, single, star-shaped.

*Flower aspect*.—Upright to outward.

*Flower bud*.—Obovate in shape, 1.2 cm in length, 1 cm in diameter, surface is smooth slightly glossy, and glabrous, 145D in color.

*Tepals*.—5, whorled in 1 row, un-fused, 3.3 cm in length, 4 mm in width, narrow elliptic to narrow oblanceolate in shape, moderately curled backwards, apex narrow acute, base narrow attenuate, margins entire, both surfaces smooth, glabrous, non- rugose, both surfaces slightly glossy, when opening upper surface; 157C to 157D, when opening lower surface; 157B, fully open upper surface; NN155D and fully open lower surface; NN155C with venation NN155B.

*Calyx*.—Rotate, 6.0 mm in length, 1.2 cm in diameter.

*Pedicels*.—5 mm in length, 1.75 mm in diameter, average of 25° angle to lateral branch (varying between vertical and)50° , moderately strong, 145C in color, surface is very slightly glossy and moderately covered with soft hairs; an average of 1 mm in length, 155C in color.

Reproductive organs:

*Gynoecium*.—Pistil; 1, stigmas; club-shaped, 144B in color, 1.5 mm in length, 2 mm in diameter, style; average 2.45 cm in length, color; 150D, distal end 154D, ovary; 143A in color, densely covered with soft hairs, 1.5 mm in length, NN155D in color.

*Androecium*.—Stamens; 10, filaments; 2.3 cm in length, NN155B in color, anthers; dorsifixed, obovate in shape, 2 mm in length, 1 mm in width, 164C to 164D in color; pollen; 156D in color, low in quantity.

*Fruit/seeds*.—No fruit or seed observed.

It is claimed:

1. A new and distinct cultivar of *Rhododendron* plant named 'AZAARE03' as herein illustrated and described.

* * * * *